(12) United States Patent
Valko et al.

(10) Patent No.: US 10,085,649 B1
(45) Date of Patent: Oct. 2, 2018

(54) METHODS AND DEVICES FOR LOCALIZING THE BLOOD MASS OF AN INTRACEREBRAL HEMATOMA

(71) Applicant: Rebound Therapeutics Corporation, Irvine, CA (US)

(72) Inventors: Jeffrey J. Valko, Irvine, CA (US); Michael R. Henson, Irvine, CA (US)

(73) Assignee: Rebound Therapeutics Corporation, Irvine, CA (US)

( * ) Notice: Subject to any disclaimer, the term of this patent is extended or adjusted under 35 U.S.C. 154(b) by 99 days.

(21) Appl. No.: 15/239,722

(22) Filed: Aug. 17, 2016

Related U.S. Application Data

(60) Provisional application No. 62/206,115, filed on Aug. 17, 2015.

(51) Int. Cl.
*A61B 5/1473* (2006.01)
*A61B 1/06* (2006.01)
*A61B 5/02* (2006.01)
*A61B 5/145* (2006.01)
*A61B 5/00* (2006.01)

(52) U.S. Cl.
CPC ............ *A61B 5/02007* (2013.01); *A61B 1/06* (2013.01); *A61B 5/1473* (2013.01); *A61B 5/14532* (2013.01); *A61B 5/6848* (2013.01); *A61B 5/6868* (2013.01); *A61B 5/6886* (2013.01); *A61B 5/742* (2013.01)

(58) Field of Classification Search
CPC ... A61B 5/02007; A61B 1/06; A61B 5/14532; A61B 5/1473; A61B 5/6848; A61B 5/6868; A61B 5/6886; A61B 5/742

USPC .......................................... 600/309, 345–366
See application file for complete search history.

(56) References Cited

U.S. PATENT DOCUMENTS

| | | | |
|---|---|---|---|
| 7,455,666 B2* | 11/2008 | Purdy | A61B 17/12113 604/506 |
| 7,787,954 B2* | 8/2010 | Purdy | A61B 17/12113 600/347 |
| 8,131,353 B2* | 3/2012 | Purdy | A61B 17/12113 128/898 |
| 8,961,452 B2* | 2/2015 | Purdy | A61B 17/12113 604/30 |
| 2003/0014016 A1* | 1/2003 | Purdy | A61B 17/12113 604/174 |
| 2009/0076357 A1* | 3/2009 | Purdy | A61B 17/12113 600/347 |
| 2010/0324397 A1* | 12/2010 | Purdy | A61B 17/12113 600/364 |
| 2012/0165757 A1* | 6/2012 | Purdy | A61B 17/12113 604/246 |
| 2015/0367105 A1* | 12/2015 | Purdy | A61B 17/12113 604/506 |
| 2016/0250451 A1* | 9/2016 | Purdy | A61B 17/12113 604/506 |
| 2017/0332887 A1* | 11/2017 | Davis | A61B 1/05 |
| 2017/0332912 A1* | 11/2017 | Tsukashima | A61B 5/0086 |

* cited by examiner

*Primary Examiner* — Navin Natnithithadha
(74) *Attorney, Agent, or Firm* — K David Crockett, Esq.; Crockett & Crockett, PC

(57) ABSTRACT

Devices as described herein for localizing an intracerebral hematoma or blood mass in brain tissue include a cannula and one or more sensor wires operably connected between a glucose meter and one or more glucose sensors for determining the location and margins of an intracerebral blood mass.

4 Claims, 3 Drawing Sheets

METHODS AND DEVICES FOR LOCALIZING THE BLOOD MASS OF AN INTRACEREBRAL HEMATOMA

This application claims priority to U.S. Provisional Patent Application 62/206,115 filed Aug. 17, 2015.

FIELD OF THE INVENTIONS

The inventions described below relate to the field of minimally invasive brain surgery.

BACKGROUND OF THE INVENTIONS

Stroke is a common cause of death and disabling neurologic disorder. Approximately 700,000 patients suffer from stroke in the United States every year. Hemorrhagic stroke accounts for 20% of the annual stroke population. Hemorrhagic stroke is due to a rupture of a blood vessel in the brain, causing bleeding into the brain tissue and resulting in a hematoma (a blood mass) in the brain. Prompt removal of the blood mass is necessary to limit or prevent long-term brain injury.

SUMMARY

The device described below for identifying the location and dimensions of a blood mass in a patient's brain includes a glucose meter, a cannula and one of more sensor wires. The sensor wire has a distal end and a proximal end and the proximal end of the sensor wire is operatively connected to the glucose meter and the distal end of the sensor wire is operatively connected to a glucose sensor. The cannula has a distal end and a proximal end and a lumen to permit access to the blood mass or other tissue of interest. In use, a surgeon extends the distal end of the sensor wire through the cannula lumen and the distal end of the sensor wire and the glucose sensor may be advanced beyond the distal end of the cannula.

The method described below for localizing a blood mass in a patient's brain uses a glucose meter, a glucose sensor, a cannula and a sensor wire. The sensor wire has a distal end and a proximal end and the proximal end of the sensor wire is operatively connected to the glucose meter and the distal end of the sensor wire is operatively connected to the glucose sensor. The cannula has a distal end and a proximal end and a lumen to permit access to the blood mass or other tissue of interest. The sensor wire extends through the cannula lumen with the distal end of the sensor wire and the glucose sensor extends beyond the distal end of the cannula. The distal end of the cannula, the distal end of the sensor wire and the glucose sensor are inserted into the patient's brain. The sensor wire is advanced until the glucose meter indicates the glucose sensor is within the blood mass. The sensor wire is further advanced until the glucose meter indicates that the glucose sensor has passed out of the blood mass. Then the cannula is advanced over the sensor wire until the distal end of the cannula is within the blood mass and the blood mass may be removed through the cannula lumen using any suitable technique.

DETAILED DESCRIPTION OF THE INVENTIONS

Figure 1:
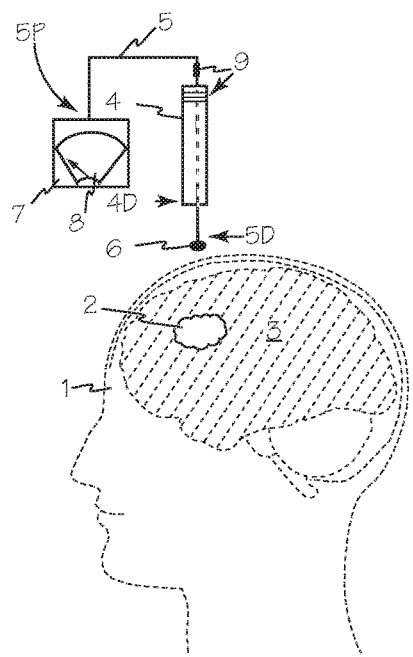
FIG. 1 is an illustration of the use of a cannula and sensor wire to localize an intracerebral blood mass in the head of a patient.
Figure 7:
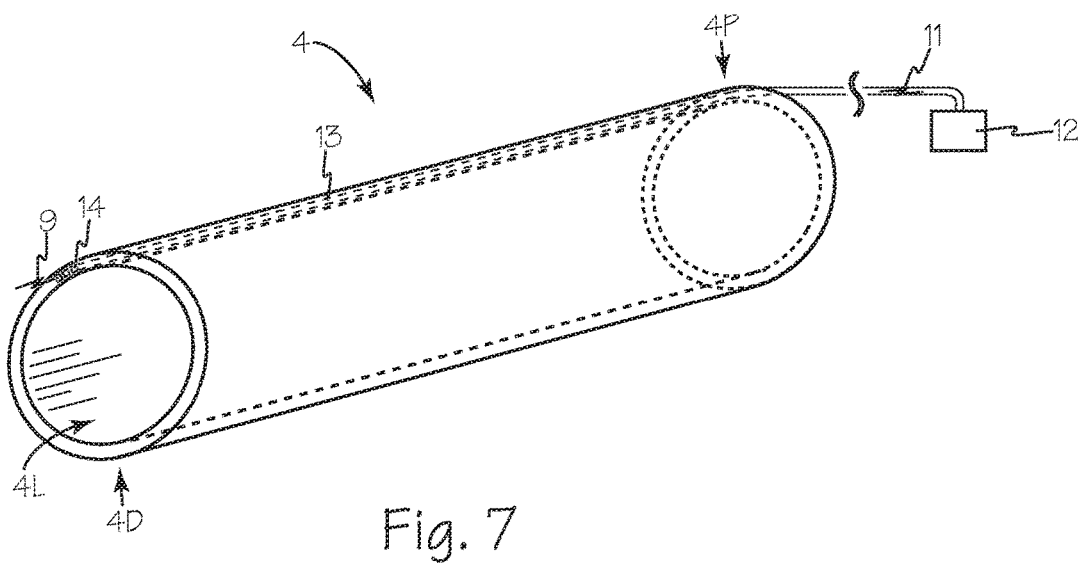
FIG. 7 is a perspective view of a localizing cannula.

FIG. 1 illustrates a patient 1 with an intracerebral hematoma or blood mass 2 in brain tissue 3 and a system for locating the intracerebral hematoma and inserting a cannula 4 into the hematoma. Cannula 4 has a distal end 4D, a proximal end 4P and a lumen 4L extending from distal end 4D to proximal end 4P as illustrated in FIG. 7. In use, a surgeon advances one or more sensor wires such as sensor wire 5 with a glucose sensor 6 disposed on the distal tip of the sensor wire through the cannula to locate and determine the size of blood mass 2. Distal end 5D includes any suitable sensor for the detection of glucose such as sensor 6. Proximal end 5P of sensor wire 5 is operatively connected to any suitable sensor display such as glucose meter 7 with a display 8 which varies according to the glucose levels detected by sensor 6. Display 8 may provide any suitable indication of glucose readings using analog, digital or audio output. Cannula 4 and sensor wire 5 may also include any suitable indicia such as indicia 9 to indicate their depth of insertion. In use, a surgeon may localize an intracerebral blood mass using one or more sensor wires to locate and map the extent of the blood mass, and then use each sensor wire as a guide wire to guide the insertion of the cannula into the blood mass.

Figure 2:
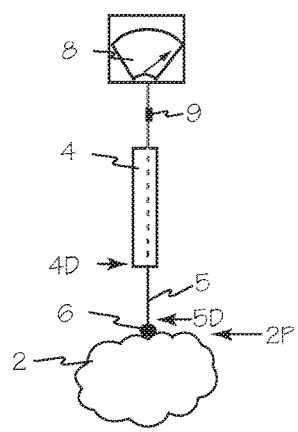
FIGS. 2 through 6 illustrate steps for localizing and removing the intracerebral blood mass from the patient of FIG. 1.
Figure 3:
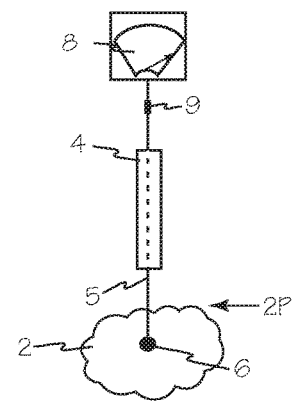
Figure 4:
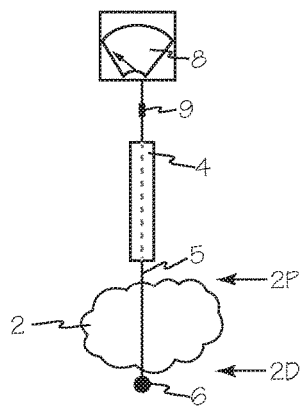
Figure 5:
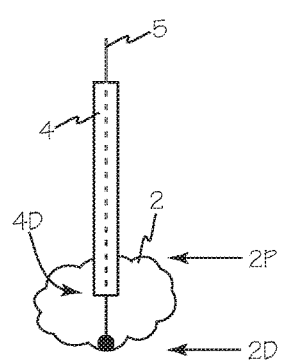
Figure 6:
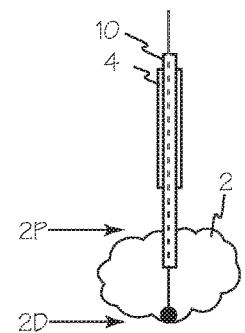

FIGS. 2 through 6 illustrate steps for localizing and removing the intracerebral blood mass from the patient of FIG. 1. In use, a surgeon or other suitable person inserts the distal end of the sensor wire 5 with glucose sensor 6 to find and localize blood mass 2. The surgeon advances cannula 4 and sensor wire 5 through brain tissue 3 until display 8 indicates that glucose sensor 6 has encountered glucose indicative of the presence of blood mass 2 as illustrated in FIG. 2. Indicia 9 is noted to identify proximal margin 2P of the blood mass. As illustrated in FIG. 3 display 8 indicates the presence of glucose when glucose sensor 6 is within blood mass 2. As sensor wire 5 and glucose sensor 6 are advanced through the blood mass the sensor will eventually exit the blood mass as illustrated in FIG. 4. When glucose sensor 6 exits the blood mass and reenters brain tissue 3 display 8 indicates a drop in glucose level and the indicia 9 on wire 5 may be noted to identify the location of the distal margin 2D of the blood mass. Once the proximal and distal margins of the blood mass, margins 2P and 2D respectively, are identified any suitable technique for removing the blood mass may be used. For example as shown in FIGS. 5 and 6 a surgeon may advance cannula 4 along wire 5 until distal end 4D is between the distal and proximal margins of blood mass 2 and then remove the blood mass through the cannula. Alternatively, a surgeon may advance a catheter 10 or other suitable instrument having a smaller diameter than cannula 4 through the cannula until the distal end 10D of the catheter is between the distal and proximal margins of the blood mass 2. Once the surgeon has located the distal end of the device for evacuating the blood mass within blood mass 2, the blood mass may be evacuated.

Figure 8:
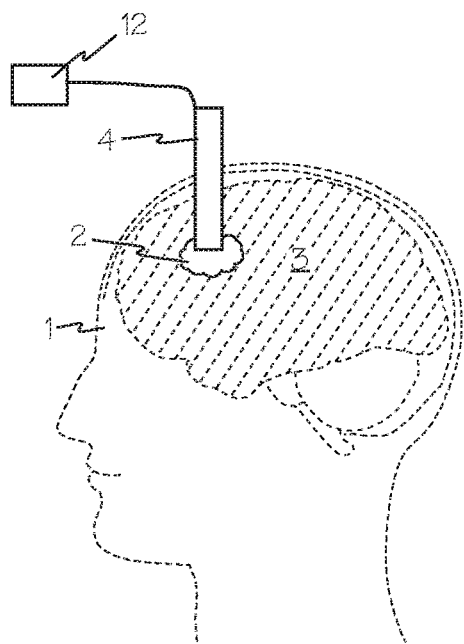
FIG. 8 is an illustration of the use of a localizing cannula in the patient of FIG. 1.
Figure 9:
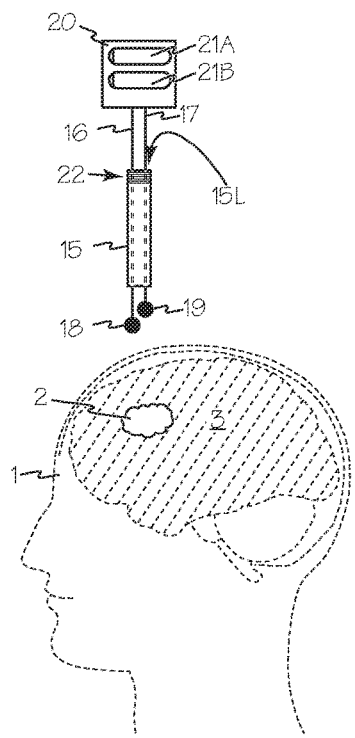
FIG. 9 is an illustration of the use of a cannula and dual sensor wires to localize an intracerebral blood mass in a patient.

FIG. 7 illustrates a cannula 4, comprising a transparent cannula that conducts light from proximal end 4P to distal end 4D. Light 11 from light source 12 couples to proximal end 4P using any suitable technique and light 11 travels from proximal end 4P to distal end 4D through the acrylic of cannula 4 or through one or more embedded light conductors or optical fibers such as fiber 13. Light of any suitable wavelength or combination of wavelengths may be directed from the cannula or embedded fibers using lenses such as lens 14. As illustrated in FIG. 8, a surgeon may extract an intracerebral blood mass through bore or lumen 4L in the cannula 4. Light sources such as light emitting diodes or other suitable elements may be incorporated into the any suitable portion of the cannula to illuminate the distal end of the cannula and the operating space surrounding the distal end of the cannula to enable localization and removal of the intracerebral blood mass.

FIGS. 9 through 12 illustrate use of a pair of sensor wires with sensor tips to determine the margins of the blood mass. The surgeon inserts cannula 15 into brain tissue to guide the insertion of first sensor wire 16 and second sensor wire through lumen 15L to find and localize blood mass. Sensor wires 16 and 17 include any suitable glucose sensor such as first glucose sensor 18 and second glucose sensor 19. First and second sensor wires 16 and 17 are operatively connected to any suitable sensor display such as glucose meter 20 with first and second displays 21A and 21B which varies according to the glucose levels measured by sensor first and second glucose sensors 18 and 19 respectively. Glucose meter 20 may provide any suitable indication of glucose readings using analog, digital or audio output. Cannula 15 and sensor wires 16 and 17 may also include any suitable indicia such as indicia 22 to indicate their depth of insertion.

Figure 10:
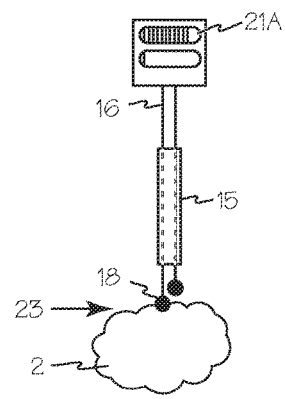
FIGS. 10 through 13 illustrate steps for localizing and removing the intracerebral blood mass from a patient.
Figure 11:
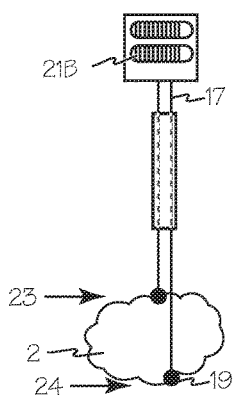
Figure 12:
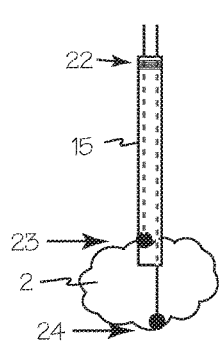
Figure 13:
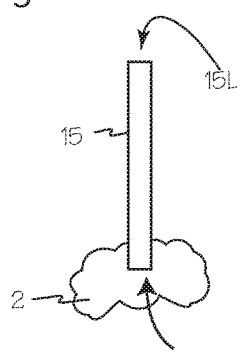

In use, a surgeon inserts the distal end of a cannula, catheter or cannula such as cannula 15 into brain tissue 3 to guide the insertion of sensor wires 16 and 17 with glucose sensors 18 and 19 through lumen 15L to find and localize blood mass 2 as illustrated in FIGS. 10, 11 and 12. First sensor wire 16 is advanced until first sensor 18 detects glucose and first display 21A indicates the presence of glucose. Upon detection of glucose, indicia 22 for first sensor wire 16 may be recorded and the first sensor wire may be immobilized or otherwise fixed relative to the position of the blood mass. The position of first sensor 18 is at the proximal margin 23 of blood mass 2. Second sensor wire 17 is advanced until second glucose sensor 19 detects glucose and second display 21B indicates the presence of glucose. Second sensor wire 17 is advanced until second display 21B indicates that second glucose sensor has detected distal margin 24 of blood mass. Indicia 22 for second sensor wire 17 may be recorded and the second sensor wire may be immobilized or otherwise fixed relative to the position of the blood mass and second sensor wire may be secured to first sensor wire 16.

Once the proximal and distal margins, margins 23 and 24 respectively, are determined, any suitable technique for evacuating blood mass 2 may be used. Cannula 15 may be advanced along the first and second sensor wires until the cannula indicia indicates that the distal end of the cannula, distal end 15D is located between the proximal and distal margins of the blood mass. Upon properly locating the cannula the sensor wires and glucose sensors may or may not be removed and then the blood mass may be evacuated through cannula lumen 15L using any suitable device or simply suction.

In the context of this application, localize or localization means to find or identify the location and extent of something such as an intracerebral blood mass in brain tissue.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A method for localizing a blood mass in a patient's brain comprising the steps:
   providing a glucose meter;
   providing a cannula having a distal end and a proximal end and a lumen;
   providing a first sensor wire having a distal end and a proximal end and the proximal end of the first sensor wire is operatively connected to the glucose meter and the distal end of the first sensor wire is operatively connected to a first glucose sensor;
   inserting the distal end of the first sensor wire into the lumen;
   inserting the distal end of the cannula and the first sensor wire and the first glucose sensor into the patient's brain;
   advancing the first sensor wire until the glucose meter indicates the first glucose sensor is within the blood mass;
   continuing to advance the first sensor wire until the glucose meter indicates that the first glucose sensor has passed out of the blood mass;
   advancing the cannula over the first sensor wire until the distal end of the cannula is within the blood mass; and
   removing the blood mass.

2. The method of claim 1 wherein the first sensor wire and first glucose sensor are withdrawn from the cannula after advancing the cannula over the first sensor wire and before the step of removing the blood mass.

3. A method for localizing a blood mass in a patient's brain comprising the steps:
   providing a glucose meter;
   providing a cannula having a distal end and a proximal end and a lumen;
   providing a first sensor wire having a distal end and a proximal end and the proximal end of the first sensor wire is operatively connected to the glucose meter and the distal end of the first sensor wire is operatively connected to a first glucose sensor;
   providing a second sensor wire having a distal end and a proximal end and the proximal end of the second sensor wire is operatively connected to the glucose meter and the distal end of the second sensor wire is operatively connected to a second glucose sensor;
   inserting the distal end of the first and second sensor wires into the lumen;
   inserting the distal end of the cannula and the first and second sensor wires and the first and second glucose sensors into the patient's brain;
   advancing the first sensor wire until the glucose meter indicates the first glucose sensor is within the blood mass;

advancing the second sensor wire until the glucose meter indicates that the second glucose sensor has passed out of the blood mass;

advancing the cannula over the first and second sensor wires until the distal end of the cannula is between the first and second glucose sensors; and removing the blood mass.

4. The method of claim 3 wherein the first and second sensor wires and the first and second glucose sensors are withdrawn from the cannula after advancing the cannula over the first and second sensor wires and before the step of removing the blood mass.

* * * * *